(12) United States Patent
Glad et al.

(10) Patent No.: US 9,433,923 B2
(45) Date of Patent: Sep. 6, 2016

(54) CHROMATOGRAPHY MEDIA AND USE THEREOF

(71) Applicant: GE Healthcare Bio-Sciences AB, Uppsala (SE)

(72) Inventors: Gunnar Glad, Uppsala (SE); Therese Graner, Uppsala (SE); Nils Norrman, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 0 days.

(21) Appl. No.: 14/407,892

(22) PCT Filed: Jun. 11, 2013

(86) PCT No.: PCT/SE2013/050662
§ 371 (c)(1),
(2) Date: Dec. 12, 2014

(87) PCT Pub. No.: WO2013/187831
PCT Pub. Date: Dec. 19, 2013

(65) Prior Publication Data
US 2015/0151276 A1    Jun. 4, 2015

(51) Int. Cl.
| | | |
|---|---|---|
| *C12Q 1/00* | (2006.01) | |
| *B01J 20/291* | (2006.01) | |
| *C07K 1/22* | (2006.01) | |
| *B01D 15/38* | (2006.01) | |
| *B01J 20/288* | (2006.01) | |
| *B01J 20/32* | (2006.01) | |
| *B01J 20/28* | (2006.01) | |
| *B01J 20/26* | (2006.01) | |
| *C12N 9/10* | (2006.01) | |

(52) U.S. Cl.
CPC .......... *B01J 20/291* (2013.01); *B01D 15/3804* (2013.01); *B01D 15/3885* (2013.01); *B01J 20/265* (2013.01); *B01J 20/288* (2013.01); *B01J 20/28009* (2013.01); *B01J 20/3212* (2013.01); *B01J 20/3251* (2013.01); *B01J 20/3274* (2013.01); *C07K 1/22* (2013.01); *C12N 9/1088* (2013.01); *B01D 2015/3838* (2013.01); *B01J 2220/80* (2013.01); *C07K 2319/23* (2013.01)

(58) Field of Classification Search
CPC ...................................................... B01J 20/291
See application file for complete search history.

(56) References Cited

U.S. PATENT DOCUMENTS

| | | | | |
|---|---|---|---|---|
| 5,632,994 A | * | 5/1997 | Reed .................. | C07K 14/4747 424/185.1 |
| 2004/0005638 A1 | | 1/2004 | Honma et al. | |
| 2008/0108123 A1 | | 5/2008 | Imamura et al. | |
| 2010/0169988 A1 | * | 7/2010 | Kohli ................. | A01K 67/0275 800/3 |

FOREIGN PATENT DOCUMENTS

| | | |
|---|---|---|
| EP | 0266580 A2 | 11/1988 |
| GB | 2195344 A | 4/1988 |
| WO | 2004056473 A1 | 7/2004 |
| WO | 2006112771 A1 | 10/2006 |
| WO | 2009/128649 A2 | 10/2009 |

OTHER PUBLICATIONS

International Search Report and Written Opinion for International Application PCT/SE2013/050682 mailed Sep. 16, 2013.
Brocklehurst K et al., "Preparation of Fully Active Papain From Dried Papaya Latex", Biochem. J., (1973), vol. 133, pp. 573-584.
Boschettie "Advanced sorbents for preparative 1-9 protein separation purposes", Journal of Chromatography A, (1994), vol. 658, pp. 207-236.
Smith DB et al "Single-step purification of polypeptides expressed in *Escherichia coli* as fusions with glutathione Stransferast", 1988, vol. 67, pp. 31-40.
Cuatrecasas P, "Protein purification by Affinity Chromatography", J of Bio Chem; (1970). vol. 245, pp. 3059-3065.
European Supplementary Search Report for EP Application No. 13803586 mailed Mar. 10, 2016 (7 pages).

* cited by examiner

*Primary Examiner* — Albert Navarro
(74) *Attorney, Agent, or Firm* — Sutherland Asbill & Brennan LLP

(57) ABSTRACT

The present invention relates to a novel non-cross linked chromatography media provided with glutathione ligands which may or may not be provided with magnetic particles. The chromatography media is used for production of an affinity media provided with gluthatione ligands for adsorption of GST-tagged proteins.

4 Claims, 2 Drawing Sheets

CHROMATOGRAPHY MEDIA AND USE THEREOF

CROSS-REFERENCE TO RELATED APPLICATIONS

This is a national stage application under 35 U.S.C. §371(c) of prior-filed, co-pending, PCT application serial number PCT/SE2013/050662, filed on Jun. 11, 2013, which claims priority to Swedish patent application serial number 1250625-9, filed on Jun. 14, 2012, the entire contents of which are incorporated by reference herein.

FIELD OF THE INVENTION

The present invention relates to a novel chromatography media and use thereof. More closely it relates to a method for coupling of GSH to a non cross-linked chromatographic media provided with magnetic particles.

BACKGROUND OF THE INVENTION

The use of affinity tags that are genetically coded and linked to a target protein to facilitate its purification is well established in the research community. Examples of commonly used such tags are glutathione-S-transferase (GST), hexa-histidine and maltose binding protein. In order to purify the affinity tagged protein, chromatography media with an immobilized specific ligand for the affinity tag is used. The chromatography media used should exhibit a high binding capacity for the target protein and yield highly pure target protein at high recoveries in a short time frame ("quality criteria"). Chromatography media used for this purpose is often in the form of beads but can also be monolithic or in other formats. Magnetic chromatography media is useful for many applications and has a number of benefits related to the purification of affinity tagged proteins. One benefit is that the magnetic bead format, in contrast to commonly used column formats, works well with samples that contain small particles like cell debris. Such small particles are often present in cell lysates which is a common start material for purification of tagged proteins. Another benefit is that purification of tagged proteins with magnetic chromatography media can be performed rapidly with very simple equipment, and with little effort. Yet another benefit is that protocols using magnetic chromatography media readily can be automated.

Magnetic chromatography media can be produced by immobilization of the desired ligand directly on an iron-containing mineral, but it is preferred to have the iron-containing mineral coated with e.g., a polymer that is inert and allows for control of the ligand density obtained during the coupling reaction. Commercially available products like His Mag Sepharose™ Ni and Streptavidin Mag Sepharose (GE Healthcare Biosciences AB) uses highly cross-linked agarose for the coating to which the ligand is attached. Such highly cross-linked agarose is also used in conventional (i.e., non-magnetic) chromatography media. For unknown reasons, magnetic chromatography media with highly cross-linked agarose and immobilized glutathione (for purification of GST-tagged proteins) does not fulfill all the quality criteria outline above. More specifically, such media exhibits a low binding capacity for GST-tagged target proteins.

SUMMARY OF THE INVENTION

In a first aspect the present invention provides a novel chromatography media which is non-crosslinked and provided with glutathione ligands.

Optionally the chromatography media may be provided with magnetic particles for easy handling in a desirable format.

The chromatography may be of natural or synthetic origin, but is preferably based on a natural plysaccharide, such as agarose, In a second aspect, the invention provides use of the above non-cross linked chromatography media for production of an affinity media provided with gluthatione ligands for adsorption of GST-tagged proteins.

The media may be provided with magnetic particles and is preferably based on agarose, most preferably Sepharose™.

In one embodiment of the invention the GST tagged proteins are fed directly after cell culture to the chromatography media. Optionally but not necessarily the GST tagged proteins are concentrated after cell culture before loading onto the chromatography media.

DETAILED DESCRIPTION OF THE INVENTION

Figure 1:
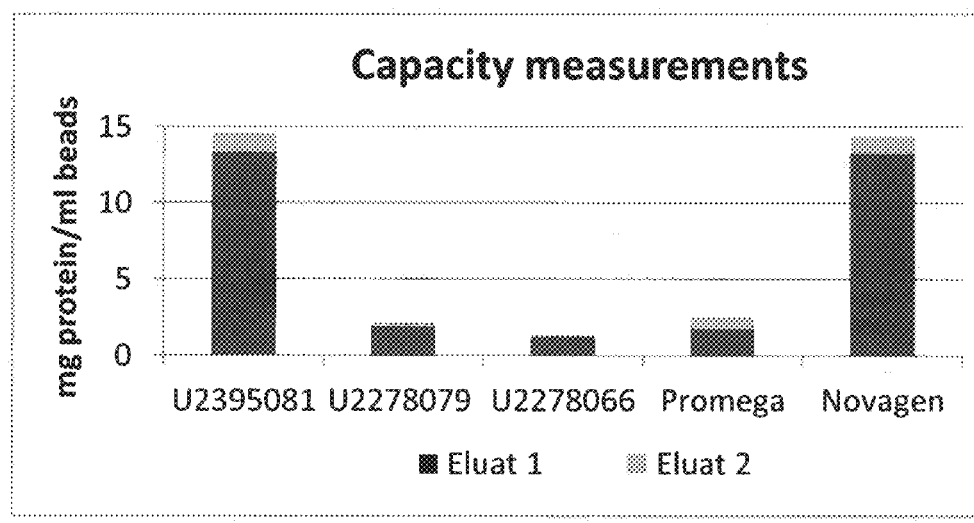
FIG. 1 shows absorbance measurements at 280 nm and 310 nm for different beads. The prototype U2395081 is GST non crosslinked magnetic Sepharose and the prototypes U2278079 and U2278066 are GST crosslinked magnetic Sepharose Also two commercial beads are shown for comparison. Capacity was compared by purifying 300 µl GST-hippocalcin in *E. coli* lysate using 25 µl magnetic beads. The five wash fractions (W1-W5) and the two elution fractions (E1-E2) were evaluated by absorbance measurements.

The invention will now be described more closely in association with a non-limiting example. In the invention a practical evaluation was performed of a new GST Mag Sepharose prototype, which has been prepared by coupling glutathione on non-crosslinked Mag Sepharose.

Example 1

Synthesis of Non-Cross Linked Mag Sepharose Prototype 18 mL of drained non cross linked Mag Sepharose is mixed and stirred with 7.5 mL 0.6M NaOH at RT. After 5 minutes, 4.5 mlL of butane-1,4-diglycidylether is added and the reaction slurry is stirred for 3 h at RT, followed by extensive washings with distilled water on a glass filter.

The drained gel is mixed with Glutathione solution (600 mg Glutathione dissolved in 15 mL distilled water, pH adjusted to 8.3 with 4M NaOH) and stirred for 18 h at RT, followed by washings on a glass filter with 0.5M NaCl and distilled water.

The media is preferably used for small scale purification of GST-tagged proteins.

GST Mag Sepharose is based on non cross linked emulsified agarose beads.

Agarose, water and magnetite is dissolved at 90° C. and emulsified in toluene and ethylencellulose at 60° C. then cooling at 40° C.

Example 2

Comparative Study

The capacity of the new GST Mag Sepharose prototype (non-crosslinked Mag Sepharose) as well as of GST Mag Agarose Beads from Novagen, MagneGST Particles from Promega and of two previously tested GST Mag Sepharose prototypes (crosslinked Mag Sepharose) were compared by purifying an overload of GST-hippocalcin in *E. coli* lysate.

Materials/Investigated Units

GST Mag Sepharose prototypes and commercially available magnetic beads.

Novagen-GST-Mag Agarose Beads; 71084; lot M00062032. Promega-MagneGST Protein, 25% v/v suspension. 5-10 mg GST-Tag fusion proteins per 1 ml settled resin. (Particle size: 1-10 microns). (Novagen)

Promega-MagneGST Glutathione Particles; V861A, lot 26785004 (278568 on package). 50% v/v suspension. 2 mg GST-Tag fusion proteins per 1 ml settled resin. (Particle size: 1-5 microns) (Promega)

Chemicals

| PBS | Medicaco 09-9400-100; Lot 140506 |
|---|---|
| Trizma-HCl 1M, pH 8.0 (Tris) | SIGMA T-2694; Lot 085K8407 |
| Reduced glutathione | Intern rek. 30215600; To nr 23977; Lot 149250-1 |

Buffers

Binding Buffer: PBS

One PBS-tablet was dissolved in 1 liter of Milli-Q water.

Elution buffer: 50 mM Tris-HCl, 10 mM reduced glutathione, pH 8.0

The buffer was prepared by dissolving 5 ml Tris-HCl and 0.303 g reduced glutathione in approximately 90 ml Milli-Q water. The pH was adjusted to 8.0 and the volume was adjusted to 100 ml.

Samples

GST hippocalcin in PBS, sonicated 26/9-2007, fermented 30/7-2005. Concentration is at least 1.5 mg/ml. Sample is labeled: 26 Sep. 2007/TG.

Methods

Sample Preparation

GST-tagged hippocalcin in *E. coli*, sonicated in September 2007 (See U2013: 49-50) was thawed and filtered using 0.45 µm filter.

Purification Protocol

All purifications were performed using PBS as binding buffer and 50 mM Tris-HCl, 10 mM reduced glutathione, pH 8.0 as elution buffer. The same purification protocol was used all media:

Magnetic bead preparation

Gently mix the bottle

Transfer 25 µl beads to 1.5 ml tube and remove storage solution

Equilibration (perform this step 3 times totally)

Add 300 µl binding buffer.

Resuspend the medium.

Remove the liquid.

Binding of antibody

Immediately after equilibration, add 300 µl of sample.

Resuspend the medium and let incubate on a shaking platform for 40 minutes.

Remove the liquid.

Washing (perform this step 5 times totally)

Add 300 µl binding buffer.

Remove the liquid.

Elution (perform this step 2 times totally)

Add 300 µl elution buffer.

Fully resuspend the medium and let incubate for 15 minutes with occasional mixing.

Remove and collect the elution fraction.

Absorbance Measurements

The protein concentration was determined at 280 and 310 nm in a spectrophotometer and calculated according to Lambert Beer's law:

$$C = A/(b^* \epsilon)$$

Where:
C=protein concentration
A=absorbance at 280 nm-310 nm
b=path length
$\epsilon$=theoretical extinction coefficient for GST-hippocalcin: 1.258 ml/mg*cm

SDS-PAGE

SDS-PAGE was performed according to Instructions for ExcelGel SDS (#80-1310-00). Samples were thawed and mixed 1:1 with 2×NSB (reduced conditions, 10 mM Bond-Breaker TCEP Solution). The samples were heated for 5 minutes at 95° C. and 20 µl of each sample was applied on an ExcelGel SDS gradient 8-18 gel. The gel was Coomassie stained.

Results and Discussion

The capacity of a new GST Mag Sepharose prototype (non-crosslinked Mag Sepharose) was evaluated. Two GST Mag Sepharose prototypes evaluated previously (crosslinked Mag Sepharose) as well as GST Mag Agarose Beads from Novagen and MagneGST Particles from Promega were included for comparison. The media binding capacities were determined by purifying 300 µl GST-hippocalcin in *E. coli* lysate using 25 µl magnetic beads. GST-hippocalcin was added in excess to all media. The five wash fractions (W1-W5) as well as the two elution fractions (E1 and E2) were evaluated by absorbance measurements (FIG. 1). The capacity of each media was calculated (FIG. 2) and the purity of elution fractions was analyzed by Coomassie stained SDS-PAGE (FIG. 3).

Figure 2:
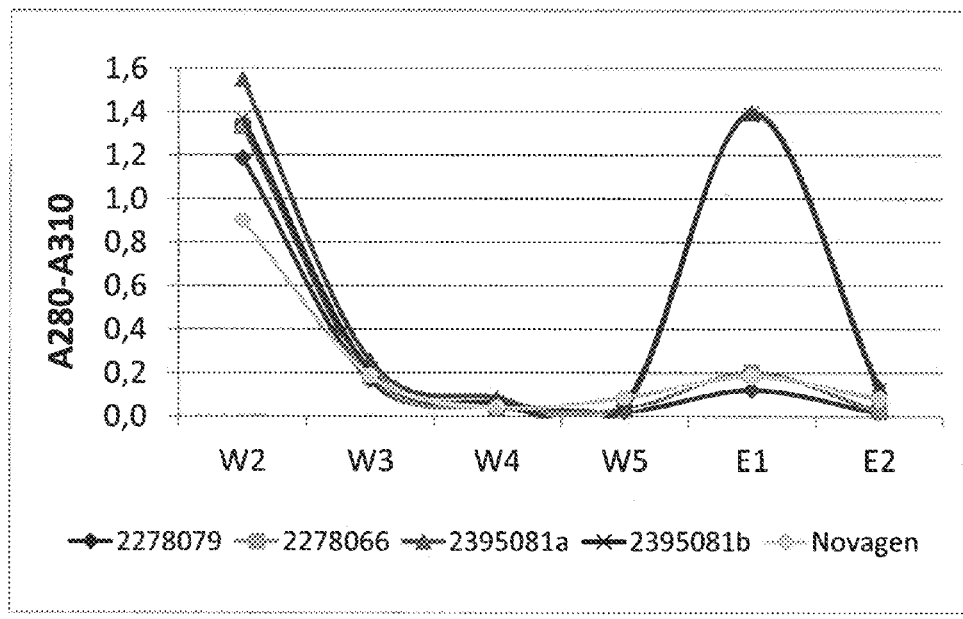
FIG. 2 shows capacity measurements. Capacity was compared by purifying 300 µl GST-hippocalcin in *E. coli* lysate using 25 µl magnetic beads. The capacity of each media, i.e. the amount of eluted sample per µl magnetic beads was calculated using Lambert Beer's law.

The absorbance measurements showed that the capacity of the new prototype was ~14.5 mg GST-Hippocalcin per 1 ml settled resin (FIG. 2). The capacity was much higher than the capacities of the prototypes prepared using crosslinked Mag Sepharose or Mag Agarose Beads from Novagen and somewhat higher using MagneGST Particles from Promega. Note: The protein eluted from MagneGST Particles from Promega had high absorbance at 310 nm which indicated aggregates or small particles and resulted in uncertain capacity determination.

Figure 3:
FIG. 3 shows an SDS-PAGE analysis. SDS-PAGE of eluates obtained by purification of 300 µl GST-hippocalcin in *E. coli* lysate using 25 µl magnetic beads. The electrophoresis was performed under reduced conditions using ExcelGel SDS Gradient 8-18. The gel was Coomassie stained.

The SDS-PAGE analysis showed high purity (>90% determined by visual inspection, FIG. 3). Moreover, the SDS-PAGE showed that both higher protein yield and purity was obtained using the new GST Mag Sepharose prototype than using any other of tested media.

Conclusions

The capacity of the new GST Mag Sepharose prototype U2395081 (non-crosslinked Mag Sepharose) was ~14.5 mg GST-Hippocalcin per 1 ml settled resin. The two competitor products Mag Agarose Beads from Novagen and MagneGST Particles from Promega had lower capacities. Also the two GST Mag Sepharose prototypes U2278079 and U2278066 prepared by coupling glutathione on crosslinked Mag Sepharose, displayed considerably lower capacities.

The invention claimed is:

1. A method for isolating proteins from a sample comprising:
   a. combining a sample comprising glutathione-S-transferase (GST) tagged proteins with an affinity chromatography media comprising non-crosslinked agarose coated magnetic beads having glutathione immobilized thereon; and
   b. magnetically separating the GST tagged proteins bound to the affinity media from the sample, thereby isolating the proteins from the sample.

2. The method of claim 1, wherein the GST tagged proteins are combined directly after cell culture to the chromatography media.

3. The method of claim 2, wherein the GST tagged proteins are concentrated after cell culture before combining with the chromatography media.

4. The method of claim 1, wherein the affinity chromatography media provides improved isolation of GST tagged proteins over an affinity chromatography media produced from crosslinked agarose coated magnetic beads having glutathione immobilized thereon.

* * * * *